United States Patent
Chen (12)

(10) Patent No.: US 6,379,148 B1
(45) Date of Patent: Apr. 30, 2002

(54) METHOD OF LOCATING A DENTAL IMPLANT

(76) Inventor: Cyril Chen, 18 Columbia Ave., Bergenfield, NJ (US) 07621

( * ) Notice: Subject to any disclaimer, the term of this patent is extended or adjusted under 35 U.S.C. 154(b) by 0 days.

(21) Appl. No.: 09/891,739

(22) Filed: Jun. 26, 2001

(51) Int. Cl.⁷ .............................. A61C 19/04; A61C 8/00
(52) U.S. Cl. ......................................... 433/72; 433/173
(58) Field of Search .................... 433/72, 75, 173, 433/174, 175, 176, 141

(56) References Cited

U.S. PATENT DOCUMENTS

| | | | | |
|---|---|---|---|---|
| 4,547,157 A | * | 10/1985 | Driskell | 433/173 |
| 6,083,004 A | * | 7/2000 | Misch et al. | 433/173 |
| 6,120,293 A | * | 9/2000 | Lazzara et al. | 433/173 |
| 6,254,387 B1 | * | 4/2001 | Bergstrom et al. | 433/49 |

* cited by examiner

Primary Examiner—John J. Wilson
(74) Attorney, Agent, or Firm—Donald J. Ersler

(57) ABSTRACT

A method of locating a dental implant includes a locator rod. The locator rod is threaded on one end to form a threaded end and modified on the other end to form a driving end. The threaded end is screwed into a threaded hole in the dental implant. The thread of the threaded end must mate with the threaded hole in the dental implant. Preferably, a gripping surface is formed on the driving end. The gripping surface allows the locator rod to be threaded into the dental implant with the grasp of fingers. The driving end of the locator rod may be shaped to receive a hand tool such as a ratchet to rotate thereof. Once the locator rod is threaded into the dental implant, an abutment, impression coping, or any other dental item may be slid over the locator rod. The dental item is rotated relative to the dental implant until a projection seats into a cavity. The locator rod is removed from the dental implant and the dental item is secured to the dental implant with a fastener.

8 Claims, 1 Drawing Sheet

METHOD OF LOCATING A DENTAL IMPLANT

BACKGROUND OF THE INVENTION

1. Field of the Invention

The present invention relates generally to dental implants and more specifically to a method of locating a dental implant such that a dental item may be attached thereto in an efficient manner.

2. Discussion of the Prior Art

Presently it appears there is no special method of attaching an abutment, impression coping or any other dental item to a dental implant. If the dental implant is located deep in the gum, there may be a problem locating the dental implant for attachment of the dental item. Rocking may be required to locate and seat a cavity on to a projection of the dental implant and dental item. The rocking will cause irritation to the gum surrounding the dental implant. Further, it is not uncommon for a dental implant to be cross-threaded during the attachment of a dental item due to misalignment. Cross-threading will destroy the dental implant and require replacement.

Accordingly, there is a clearly felt need in the art for a a method of locating a dental implant which allows the attachment of a dental item in an efficient manner without unnecessarily irritating the gum surrounding the dental implant or destruction of the dental implant.

SUMMARY OF THE INVENTION

The present invention provides a method of locating a dental implant for attachment of a dental item. The method of locating a dental implant includes a locator rod. The locator rod is threaded on one end to form a threaded end and modified on the other end to form a driving end. The threaded end is screwed into a threaded hole in the dental implant. The thread of the threaded end must mate with the threaded hole in the dental implant. Preferably, a gripping surface is formed on the driving end to allow finger rotation of the locating rod. The driving end could be textured or knurled to form the gripping surface. Other modifications to the driving end could also be used to facilitate finger rotation. The driving end of the locator rod may be shaped to allow a hand tool such as a ratchet to rotate thereof. Once the locator rod is threaded into the dental implant, an abutment, impression coping or any other dental item may be slid over the locator rod. The dental item is rotated until a projection mates with a cavity and then the abutment is pushed on to the dental implant until the projection seats into the cavity. The locator rod is removed from the dental implant and the dental item secured to the dental implant with a fastener.

Accordingly, it is an object of the present invention to provide a method of locating a dental implant for attachment of a dental item in an efficient manner.

It is a further object of the present invention to provide a method of locating a dental implant for attachment of a dental item which will help prevent cross-threading of the dental implant.

Finally, it is another object of the present invention to provide a method of locating a dental implant for attachment of an abutment which does not irritate the gum.

These and additional objects, advantages, features and benefits of the present invention will become apparent from the following specification.

DETAILED DESCRIPTION OF THE PREFERRED EMBODIMENTS

Figure 1:
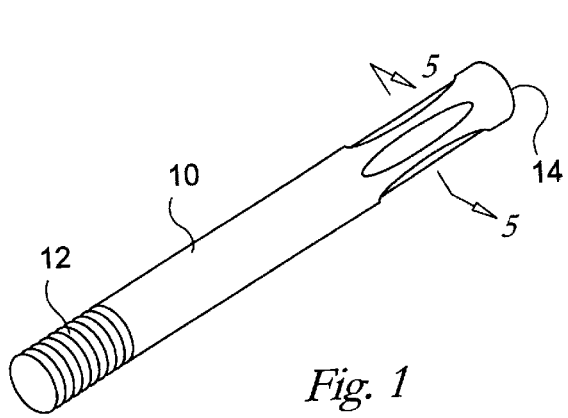
FIG. 1 is a perspective view of a locator rod of a method for locating a dental implant in accordance with the present invention.
Figure 2:
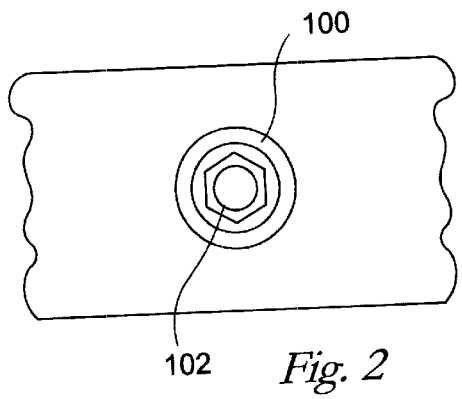
FIG. 2 is a top view of a dental implant located deep in a gum of a patient.
Figure 3:
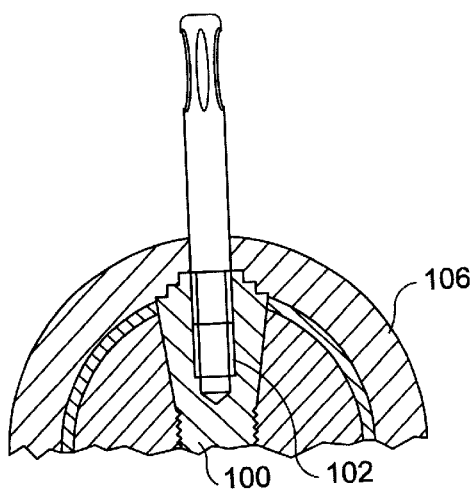
FIG. 3 is a cross sectional view of a locator rod threaded into a dental implant in accordance with the present invention.
Figure 4:
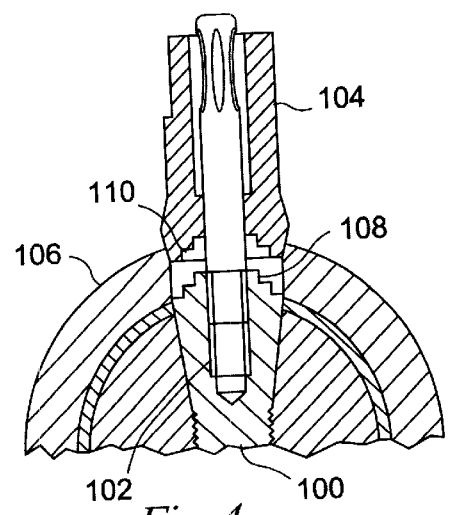
FIG. 4 is a cross sectional view of an abutment slid on to a locator rod of a method for locating a dental implant in accordance with the present invention.

With reference now to the drawings, and particularly to FIG. 1, there is shown a perspective view of a locator rod 10. The method of locating a dental implant includes the locator rod 10. With reference to FIGS. 2–4, the locator rod 10 is threaded on one end to form a threaded end 12 and modified on the other end to form a driving end 14. The locator rod 10 is threaded into a threaded hole 102 in a dental implant 100. The thread of the threaded end 12 must mate with the threaded hole 102 in the dental implant 100. Preferably, a gripping surface is formed on the driving end 14. The locator rod 10 may be fabricated from metal, plastic, or any other appropriate material. The locator rod 10 may also be fabricated by sintering metal, molding plastic, die casting or through any other appropriate process.

Figure 5:
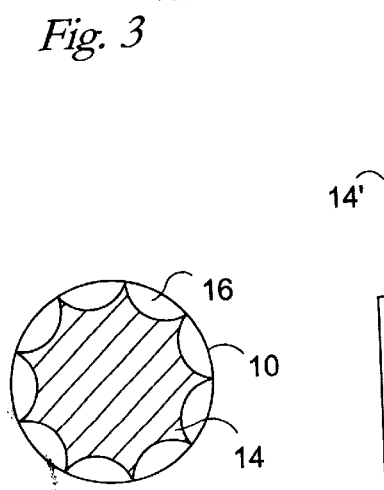
FIG. 5 is an enlarged cross sectional view of a driving end a locator rod in accordance with the present invention.
Figure 6:
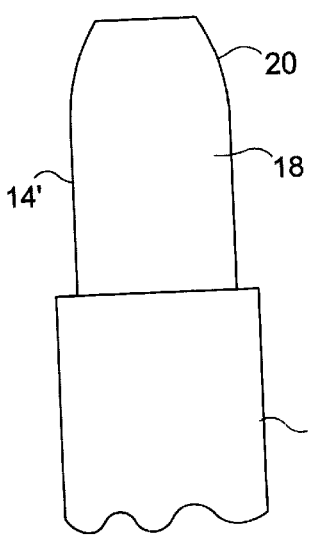
FIG. 6 is an enlarged side view of an alternative driving end a locator rod in accordance with the present invention.

The gripping surface must be machined into a solid piece of material during a secondary operation, but may be formed as part of the locator rod 10 when sintering, molding or casting. With reference to FIG. 5, the gripping surface is a deep slot knurl 16. With reference to FIG. 6, the diameter of the driving end 14' is reduced to compensate for material being displaced from the knurl cavities 18 and a diamond knurl is created as the gripping surface. It is preferable that the outside diameter of the locator rod 10, 10' be greater than the outside diameter of the driving end 14, 14'. The outer diameter of the driving end 14 is preferably less than the inner diameter of an abutment 104 to allow insertion therethrough. Two examples of knurling are shown, but other types of gripping surfaces may be used to facilitate threading by grasping with fingers, such as forming two parallel flat surfaces on the driving end 14. It is preferable to form a lead-in surface 20 on the end of the driving end 14, 14'. The lead-in surface 20 could be a bullet point, a chamfer, or any other appropriate type of lead-in surface.

Figure 7:
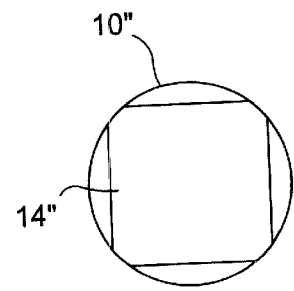
FIG. 7 is an end view of a driving end of a locator rod modified to accept rotation from a hand tool in accordance with the present invention.

It may be desirable for some to use a tool for threading the threaded end 12 into the dental implant 100. With reference to FIG. 7, the driving end 14" has a shape which is adapted to be rotated by a hand tool. The shape of driving end 14" could be a square (as shown in FIG. 7), a hex or any other suitable shape which is adapted for driving by a hand tool.

Once the locator rod 10 is threaded into the dental implant 100, the abutment 104 is slid over the locator rod 10 and pushed past the gum 106. The abutment 104 is rotated until a projection 108 of the dental implant 100 seats into a cavity 110 of the abutment 104. After the abutment 104 is seated on to the dental implant 100, the locator rod 10 is unthreaded from the dental implant 100. A fastener is then threaded into the dental implant 100 to secure the abutment 104 to the dental implant 100.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

I claim:

1. A method of locating a dental implant for attachment of a dental item thereto comprising the steps of:
   (a) providing a locator rod having a threaded end and a second end;
   (b) screwing said threaded end of said locator rod into said dental implant;
   (c) sliding a dental item on to said locator rod;
   (d) seating said dental item on to said dental implant;
   (e) removing said locator rod from said dental implant; and
   (f) securing said dental item to said dental implant.

2. The method of locating a dental implant for attachment of a dental item thereto of claim 1, wherein:
   a gripping surface being formed on said second end of said locator rod such that thereof may be rotated by fingers.

3. The method of locating a dental implant for attachment of a dental item thereto of claim 1, wherein:
   said second end of said locator rod being shaped such that thereof may be rotated by a hand tool.

4. The method of locating a dental implant for attachment of a dental item thereto of claim 1, wherein:
   a lead-in surface being formed on said driving end.

5. A method of locating a dental implant for attachment of a dental item thereto comprising the steps of:
   (a) providing a locator rod having a threaded end and a driving end, a gripping surface being formed on said driving end;
   (b) screwing said threaded end of said locator rod into said dental implant by grasping said gripping surface with fingers;
   (c) sliding a dental item on to said locator rod;
   (d) seating said dental item on to said dental implant;
   (e) removing said locator rod from said dental implant; and
   (f) securing said dental item to said dental implant.

6. The method of locating a dental implant for attachment of a dental item thereto of claim 5, wherein:
   a lead-in surface being formed on said driving end.

7. A method of locating a dental implant for attachment of a dental item thereto comprising the steps of:
   (a) providing a locator rod having a threaded end and a driving end, said driving end being shaped to receive a hand tool;
   (b) screwing said threaded end of said locator rod into said dental implant with said hand tool;
   (c) sliding a dental item on to said locator rod;
   (d) seating said dental item on to said dental implant;
   (e) removing said locator rod from said dental implant; and
   (f) securing said dental item to said dental implant.

8. The method of locating a dental implant for attachment of a dental item thereto of claim 7, wherein:
   a lead-in surface being formed on said driving end.

* * * * *